United States Patent
Lee et al.

(10) Patent No.: US 10,109,170 B2
(45) Date of Patent: *Oct. 23, 2018

(54) METHOD AND SYSTEM FOR IMPLEMENTING ALARMS FOR MEDICAL DEVICE THROUGH MOBILE DEVICE

(71) Applicant: SAMSUNG ELECTRONICS CO., LTD., Suwon-si (KR)

(72) Inventors: Jong-rip Lee, Suwon-si (KR); Hang-chan Kim, Suwon-si (KR); Sung-hwa Lee, Anyang-si (KR); Chang-sub Lee, Mokpo-si (KR); Sung-ho Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/985,824

(22) Filed: Dec. 31, 2015

(65) Prior Publication Data

US 2016/0110985 A1  Apr. 21, 2016

Related U.S. Application Data

(63) Continuation of application No. 14/186,399, filed on Feb. 21, 2014, now Pat. No. 9,230,420.
(Continued)

(30) Foreign Application Priority Data

Apr. 23, 2013 (KR) ........................ 10-2013-0044881

(51) Int. Cl.
*G08B 1/08* (2006.01)
*G08B 21/02* (2006.01)
(Continued)

(52) U.S. Cl.
CPC ............ *G08B 21/02* (2013.01); *A61B 5/0002* (2013.01); *A61B 5/0022* (2013.01);
(Continued)

(58) Field of Classification Search
CPC ............... G08B 21/02; G06F 19/3418; H04M 1/72538; A61B 5/0002; A61B 5/0022; H04B 1/3827
(Continued)

(56) References Cited

U.S. PATENT DOCUMENTS 6,494,831 B1  12/2002 Koritzinsky
6,699,195 B2  3/2004 Nakazawa et al.
(Continued)

FOREIGN PATENT DOCUMENTS

CN  1604533 A  4/2005
CN  1701335 A  11/2005
(Continued)

OTHER PUBLICATIONS

Communication dated Jun. 13, 2016, issued by the Korean Intellectual Property Office in counterpart Korean Application No. 10-2013-0044881.
(Continued)

*Primary Examiner* — John A Tweel, Jr.
(74) *Attorney, Agent, or Firm* — Sughrue Mion, PLLC

(57) ABSTRACT

Provided are a method and system for implementing alarms for a medical device through a mobile device. The method includes: storing details of examination of a specimen (hereinafter, referred to as examination details) in the medical device, wherein the storing is performed by the medical device; accessing the medical device and establishing a connection with the medical device, wherein the accessing and the establishing of the connection is performed by the mobile device; reading the examination details stored in the
(Continued)

medical device, wherein the reading is performed by the mobile device; analyzing the read examination details, wherein the analyzing is performed by the mobile device; and implementing an alarm if the result of analysis satisfies a predetermined criterion, wherein the implementing is performed by the mobile device.

17 Claims, 11 Drawing Sheets

Related U.S. Application Data

(60) Provisional application No. 61/767,978, filed on Feb. 22, 2013.

(51) Int. Cl.
| | | |
|---|---|---|
| *A61B 5/00* | (2006.01) | |
| *H04M 1/725* | (2006.01) | |
| *G06F 19/00* | (2018.01) | |
| *H04B 1/3827* | (2015.01) | |

(52) U.S. Cl.
CPC ....... *G06F 19/3418* (2013.01); *H04B 1/3827* (2013.01); *H04M 1/72538* (2013.01)

(58) Field of Classification Search
USPC .............. 340/539.12; 705/2; 455/66.1, 411
See application file for complete search history.

(56) References Cited

U.S. PATENT DOCUMENTS

| | | | |
|---|---|---|---|
| 6,735,551 | B2 | 5/2004 | Voegeli et al. |
| 8,005,947 | B2 | 8/2011 | Morris et al. |
| 8,038,593 | B2 | 10/2011 | Friedman et al. |
| 8,111,817 | B2 | 2/2012 | Hsu et al. |
| 8,630,867 | B2 | 1/2014 | Yoo |
| 8,680,974 | B2 | 3/2014 | Meiertoberens et al. |
| 9,230,420 | B2 * | 1/2016 | Lee .................. G08B 21/02 |
| 2002/0169584 | A1 | 11/2002 | Fu et al. |
| 2003/0149598 | A1 | 8/2003 | Santoso et al. |
| 2003/0153297 | A1 | 8/2003 | Falkiner et al. |
| 2004/0057340 | A1 | 3/2004 | Charles-Erickson et al. |
| 2004/0059205 | A1 | 3/2004 | Carlson et al. |
| 2004/0199056 | A1 | 10/2004 | Husemann et al. |
| 2005/0038326 | A1 | 2/2005 | Mathur |
| 2005/0102167 | A1 | 5/2005 | Kapoor |
| 2005/0192845 | A1 | 9/2005 | Brinsfield et al. |
| 2006/0036134 | A1 | 2/2006 | Tarassenko et al. |
| 2006/0284732 | A1 | 12/2006 | Brock-Fisher |
| 2007/0025877 | A1 | 2/2007 | Hansen |
| 2007/0255114 | A1 | 11/2007 | Ackermann et al. |
| 2007/0270662 | A1 | 11/2007 | Chen |
| 2008/0091175 | A1 | 4/2008 | Frikart et al. |
| 2008/0096495 | A1 | 4/2008 | Shen |
| 2008/0119705 | A1 | 5/2008 | Patel et al. |
| 2008/0242945 | A1 | 10/2008 | Gugliotti et al. |
| 2009/0105567 | A1 | 4/2009 | Smith et al. |
| 2009/0240120 | A1 | 9/2009 | Mensinger et al. |
| 2009/0273467 | A1 | 11/2009 | Elixmann et al. |
| 2010/0033332 | A1 | 2/2010 | Heath et al. |
| 2010/0081895 | A1 | 4/2010 | Zand |
| 2010/0094098 | A1 | 4/2010 | Smith et al. |
| 2010/0161003 | A1 | 6/2010 | Malmberg et al. |
| 2010/0274104 | A1 | 10/2010 | Khan |
| 2010/0298742 | A1 | 11/2010 | Perlman et al. |
| 2010/0309001 | A1 | 12/2010 | Connolly et al. |
| 2011/0015508 | A1 | 1/2011 | Peyser |
| 2011/0081888 | A1 | 4/2011 | Waniss |
| 2012/0068847 | A1 | 3/2012 | Pirzada |
| 2012/0109688 | A1 | 5/2012 | Yoo |
| 2012/0276843 | A1 | 11/2012 | Yuasa |
| 2012/0310660 | A1 | 12/2012 | Liu et al. |
| 2014/0149133 | A1 | 5/2014 | Gibby et al. |

FOREIGN PATENT DOCUMENTS

| | | |
|---|---|---|
| CN | 1816794 A | 8/2006 |
| CN | 101252465 A | 8/2008 |
| CN | 101569521 A | 11/2009 |
| CN | 101620647 A | 1/2010 |
| CN | 101821722 A | 9/2010 |
| CN | 102356625 A | 2/2012 |
| EP | 0970655 A1 | 1/2000 |
| EP | 1107159 A2 | 6/2001 |
| EP | 1400259 B1 | 7/2005 |
| EP | 2315146 A1 | 4/2011 |
| KR | 1020060124082 A | 12/2006 |
| KR | 10-0707098 B1 | 4/2007 |
| KR | 10-0783284 B1 | 12/2007 |
| KR | 1020100014065 A | 2/2010 |
| KR | 10-2010-0041660 A | 4/2010 |
| KR | 10-0975383 B1 | 8/2010 |
| WO | 2012060810 A1 | 5/2012 |

OTHER PUBLICATIONS

Communication dated Aug. 15, 2016, issued by the State Intellectual Property Office of P.R. China in counterpart Chinese Application No. 201410062465.X.
Communication dated Sep. 28, 2014 issued by Korean Intellectual Property Office in counterpart Korean Application No. 10-2013-0073314.
Communication, dated Jul. 7, 2014, issued by the European Patent Office in counterpart Patent Application No. 14156204.1.
Communication, dated Jul. 7, 2014, issued by the European Patent Office in counterpart Patent Application No. 14156203.3.
Communication dated Jun. 21, 2016, issued by the State Intellectual Property Office of P.R. China in counterpart Chinese Application No. 201410062691.8.
Tang et al: "Development and Application of Short Message Service Platform for Hospital" Chinese Medical Equipment Journal, vol. 30 No. 9, Sep. 30, 2009, pp. 46-48, (3 pages total).
Communication dated Feb. 24, 2017, issued by the State Intellectual Property Office of the People's Republic of China in counterpart Chinese Patent Application No. 201410062691.8.
Communication dated Aug. 16, 2017, issued by the State Intellectual Property Office of P.R. China in counterpart Chinese Application No. 201410062691.8.
Communication issued by the State Intellectual Property Office of P.R. China dated Oct. 26, 2017 in counterpart Chinese Patent Application No. 201410062465.X.
Communication dated Feb. 23, 2018 by the State Intellectual Property Office of P.R. China in counterpart Chinese Patent Application No. 201410062691.8.
Communication dated Jun. 5, 2018, issued by the State Intellectual Property Office of the People's Republic of China in counterpart Chinese Patent Application No. 201410062465.X.

* cited by examiner

FIG. 8

| | |
|---|---|
| | AM 12:27 |

EXAMINATION RESULT LIST

801 — EXAMINATION RESULT 8
803 — 2013/2/14 08:36:38

EXAMINATION RESULT 7
2013/2/13 17:39:32

EXAMINATION RESULT 6
2013/1/25 14:30:16

EXAMINATION RESULT 5
2013/1/25 14:18:03

EXAMINATION RESULT 4
2013/1/25 14:18:03

EXAMINATION RESULT 3
2013/1/15 19:40:44

EXAMINATION RESULT 2
2013/1/15 19:35:31

EXAMINATION RESULT 1
2013/1/15 19:25:22

FIG. 9

| | | | | |
|---|---|---|---|---|
| | EXAMNINATION RESULT 8  2013/2/14 08:36:38 ← 901 | | | |
| | ALB | Ⓐ 1.0 | 3.5-5.3 | g/dl |
| | TP | Ⓐ 2.2 | 6.0-8.5 | g/dl |
| | CHOL | Ⓐ 24 | 120-230 | mg/dl |
| | GLU | Ⓐ 13 | 70-110 | mg/dl |
| 911 → Ⓒ | BUN | Ⓐ 2.0 | 5.0-24.0 | mg/dl |
| | HDL | Ⓐ 15 | 40-140 | mg/dl |
| | TRIG | 45 | 5-200 | mg/dl |
| | LDL | 1 | 0-130 | mg/dl |

SET ALARM        [+] —1007
EXAMINATION COMPLETION   ↗—1009
OCCURRENCE OF ABNORMAL CONDITION   ↗—1011
BUN   ↗—1013

FIG. 10B

SET CRITICAL RANGE
ACOUSTIC SOUND   1005—[Bubbles ∨]
VIBRATION   1017   ↗
Critical value scope
[10]  ≤  [ALT ∨]  ≤  [300]

| 1 | 2 | 3 | ⌫ |
| 4 | 5 | 6 | CONFIRM |
| 7 | 8 | 9 | 123/SYMBOL |
| . | 0 |   | 한/영 |

SET ALARM        [+]
EXAMINATION COMPLETION   ↗
OCCURRENCE OF ABNORMAL CONDITION   ↗
BUN   ↗
ALT —1021   ↗

METHOD AND SYSTEM FOR IMPLEMENTING ALARMS FOR MEDICAL DEVICE THROUGH MOBILE DEVICE

RELATED APPLICATIONS

This is a Continuation of U.S. application Ser. No. 14/186,399, filed Feb. 21, 2014, which claims the benefit of U.S. Provisional Application No. 61/767,978, filed on Feb. 22, 2013, in the US Patent Office and Korean Patent Application No. 10-2013-0044881, filed on Apr. 23, 2013, in the Korean Intellectual Property Office, the disclosures of which are incorporated herein in their entireties by reference.

BACKGROUND

1. Field

One or more exemplary embodiments relate to a method and system for implementing alarms for a medical device through a mobile device.

2. Description of the Related Art

Ubiquitous healthcare (U-Health) integrates information technology (IT) with health and medical care to provide healthcare services such as prevention, diagnosis, treatment, and follow-up management of diseases. With dissemination of the U-Health concept, an increasing number of medical devices that are used inside or outside a hospital tend to be connected to one another via a network. However, a user of a medical device for providing examination and diagnosis functions is inconvenienced in having to stay near the medical device during the length of examination. Thus, an alarm function of a medical device has been implemented using a warning light or an acoustic sound so that a user may recognize completion of examination or occurrence of errors in the medical device even when being located away from the medical device. In addition, when necessary, alarm information of a medical device may be transmitted to a user's PC. However, an alarm using a warning light or acoustic sound has a limitation in a distance to which a user can perceive the alarm. Furthermore, in order to transmit alarm information to a PC, a connection for transmitting the alarm information has to be continuously maintained. This may not only cause the waste of medical device's communication resources but also hamper concentration of resources on an examination function that is a basic function of the medical device.

FIGS. 1A and 1B are schematic diagrams of conventional configurations in which a medical device 101 or 107 implements an alarm.

Referring to FIG. 1A, when a cause for an alarm occurs in the medical device 101, the medical device 101 notifies a user side 105 of occurrence of the cause for alarm through a warning light or speaker 103. According to this conventional method, a user is inconvenienced in having to stay within a range in which the user is able to see the warning light or perceive an alarm sound output from the speaker.

Referring to FIG. 1B, when a cause for an alarm occurs in the medical device 107, the medical device 107 transmits an alarm notification to an in-house server 109 that will then deliver the alarm notification to a user's PC 111 so that the user's PC 111 implement an alarm. However, in this case, since a connection for transmitting alarm information to the user's PC 111 has to be maintained continuously, communication resources of the medical device may be wasted, and resources cannot be concentrated in a main function, i.e., an examination function of the medical device 107.

SUMMARY

One or more exemplary embodiments include a method and system for effectively implementing alarms for a medical device through a mobile device.

One or more exemplary embodiments include a computer-readable recording medium having recorded thereon a program for executing the method on a computer.

One or more exemplary embodiments include an application for providing an alarm through a mobile device that is connected directly to a medical device.

One or more exemplary embodiments include a system configured to not only provide an alarm notifying simple examination-completion or error-occurrence but also individually set alarm conditions for each examinee. In this case, it is possible to set a range that is considered important in the result of examination of an individual examinee and process a situation that falls within the set range as emergency alarm.

Additional aspects will be set forth in part in the description which follows and, in part, will be apparent from the description, or may be learned by practice of the presented embodiments.

According to one or more exemplary embodiments, a method of implementing an alarm for a medical device through a mobile device includes: storing details of examination of a specimen (hereinafter, referred to as examination details) in the medical device, wherein the storing is performed by the medical device; accessing the medical device and establishing a connection with the medical device, wherein the accessing and the establishing of the connection is performed by the mobile device; reading the examination details stored in the medical device, wherein the reading is performed by the mobile device; analyzing the read examination details, wherein the analyzing is performed by the mobile device; and implementing an alarm if the result of analysis satisfies a predetermined criterion, wherein the implementing is performed by the mobile device.

The accessing may be performed for every predetermined period.

The connection may be maintained only while the mobile device accesses the medical device to establish the connection with the medical device and reads the examination details from the medical device.

If the result of analysis satisfies the predetermined criterion, the result of the examination of the specimen (hereinafter, referred to as an examination result) may deviate from a preset range, or the examination of the specimen may be completed.

The preset range may be set individually for each examination item of an individual examinee.

When the examination result deviates from the preset range and falls within a critical range, an alarm may be implemented, and at the same time an alarm notification may be transmitted to a predetermined destination.

The medical device may recognize a plurality of mobile devices to record therein a history that examination details have been read by each of the mobile devices and allow the mobile device to read only examination details that have not been read by the mobile device.

The alarm may be implemented as at least one of a bell sound, music, an acoustic sound, a vibration, flashing light, and a popup window.

According to one or more exemplary embodiments, a mobile device for implementing an alarm for a medical device includes: a transmitter for transmitting requests for establishing a connection with the medical device and for reading details of examination of a specimen (hereinafter, referred to as "examination details") stored in the medical device; a receiver for receiving from the medical device a response to accept the request for establishing the connection with the medical device and the examination details; a processor that analyzes the received examination details and determines whether the result of analysis of the examination details satisfies a predetermined criterion; and an alarm unit for implementing an alarm if the result of analysis satisfies the predetermined criterion.

The request for establishing the connection with the medical device may be made for every predetermined period.

The connection may be maintained only while the mobile device establishes the connection with the medical device and receives the examination details from the medical device.

If the result of analysis satisfies the predetermined criterion, the result of the examination of the specimen (hereinafter, referred to as an examination result) may deviate from a preset range, or the examination of the specimen may be completed.

The preset range may be set individually for each examination item of an individual examinee.

When the examination result deviates from the preset range and falls within a critical range, an alarm may be implemented, and at the same time an alarm notification may be transmitted to a predetermined destination.

The mobile device may be set to read only examination details that have not been read thereby.

The alarm may be implemented as at least one of a bell sound, music, an acoustic sound, a vibration, flashing light, and a popup window.

According to one or more exemplary embodiments, a medical device for implementing an alarm through a mobile device includes: a specimen inserter for inserting the specimen; an examination and processing unit that examines the specimen and processes the result of examination of the specimen (hereinafter, referred to as an examination result); a storage unit for storing the examination result; a receiver for receiving requests for establishing a connection and for reading details of the examination of the specimen (hereinafter, referred to as examination details) from the mobile device; and a transmitter for transmitting a response that accepts the request for establishing the connection together with the examination details.

The request for establishing the connection may be made for every predetermined period.

The connection may be maintained only while the mobile device establishes the connection with the medical device and receives the examination details from the medical device.

The transmitter may transmit the examination result defined as particular values or ranges of values.

When the examination result deviates from a preset range and falls within a critical range, the transmitter may transmit an alarm notification to a predetermined destination.

The medical device may recognize a plurality of mobile devices to record therein a history that the examination details have been read by each of the mobile devices and allow the mobile device to read only examination details that have not been read by the mobile device.

The mobile device may analyze the received examination details and implement an alarm if the result of analysis of the examination details satisfies a predetermined criterion.

The alarm may be implemented as at least one of a bell sound, music, an acoustic sound, a vibration, flashing light, and a popup window.

According to one or more exemplary embodiments, a non-transitory computer-readable recording medium has recorded thereon a program for executing the method on a computer.

As described above, upon completion of examination of a specimen using a medical device, or when the examination result deviates from a preset range, an alarm may be generated through a mobile device, thereby eliminating the need for an examiner to continuously stay near or an examiner's PC to be connected to the medical device during the examination. Furthermore, a connection between the mobile device and the medical device is maintained only while the mobile device accesses the medical device to establish a connection therewith and reads details of examination from the medical device, thereby reducing burden on a function of the medical device other than an examination function. In other words, the medical device may be dedicated to performing its main function, i.e., an examination function by using resources of a mobile device instead of resources of the medical device to implement an alarm function. Furthermore, when the examination result deviates from a preset range to fall within a critical range, an emergency notification may be transmitted to a predetermined destination while an alarm is being implemented, thus allowing medical personnel to immediately identify a critical condition in the examination result. Furthermore, a response to the examination result may be set differently for an individual user, thereby allowing medical personnel to more effectively respond to the examination result. In addition, it is possible to set alarms differently across a plurality of mobile devices that are connected to the medical device, thereby allowing different settings and notifications of alarms in response to the same examination result, as needed by a diagnostic staff (or a user of a mobile device).

BRIEF DESCRIPTION OF THE DRAWINGS

These and/or other aspects will become apparent and more readily appreciated from the following description of the exemplary embodiments, taken in conjunction with the accompanying drawings, and reference numerals therein denote structural elements, in which:

FIG. 8 is a schematic diagram of a screen of a mobile device that appears when an item 'view examination results' shown in FIG. 6 is selected, according to an exemplary embodiment;

FIG. 9 is a schematic diagram of a screen of a mobile device that appears when 'examination result 8' shown in FIG. 8 is selected, according to an exemplary embodiment;

FIGS. 10A through 10C are schematic diagrams of screens of a mobile device that appear when an item 'set' shown in FIG. 6 is selected, according to an exemplary embodiment;

DETAILED DESCRIPTION

The terms used in this specification are general terms currently widely used in the art in consideration of functions in regard to the present invention, but the terms may vary according to the intention of one of ordinary skill in the art, precedents, or the occurrence of new technologies in the art. Also, specific terms may be selected by the applicant, and in this case, the detailed meaning thereof will be described in the detailed description of the invention. Thus, the terms used in the specification should be understood not as simple names but based on their meanings and the overall description of the invention.

Throughout the specification, it will also be understood that when a component "includes" an element, unless there is another opposite description thereto, the component does not exclude another element but may further include another element. In addition, terms such as "... unit", "... module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Exemplary embodiments of the present invention will now be described more fully hereinafter with reference to the accompanying drawings.

Figure 1A:
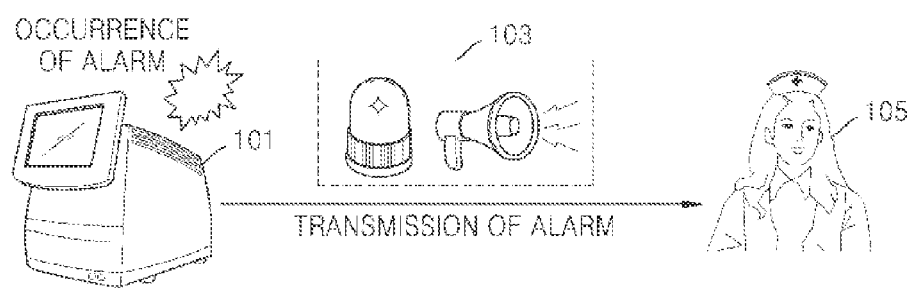
FIGS. 1A and 1B are conceptual diagrams of conventional methods of implementing alarms for medical devices.
Figure 1B:
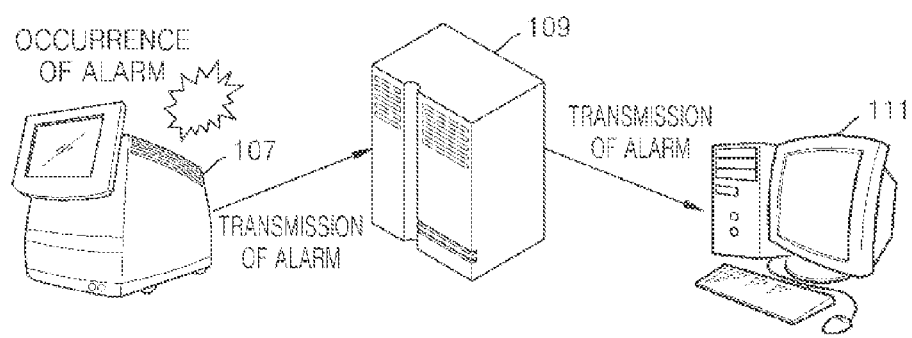
Figure 2:
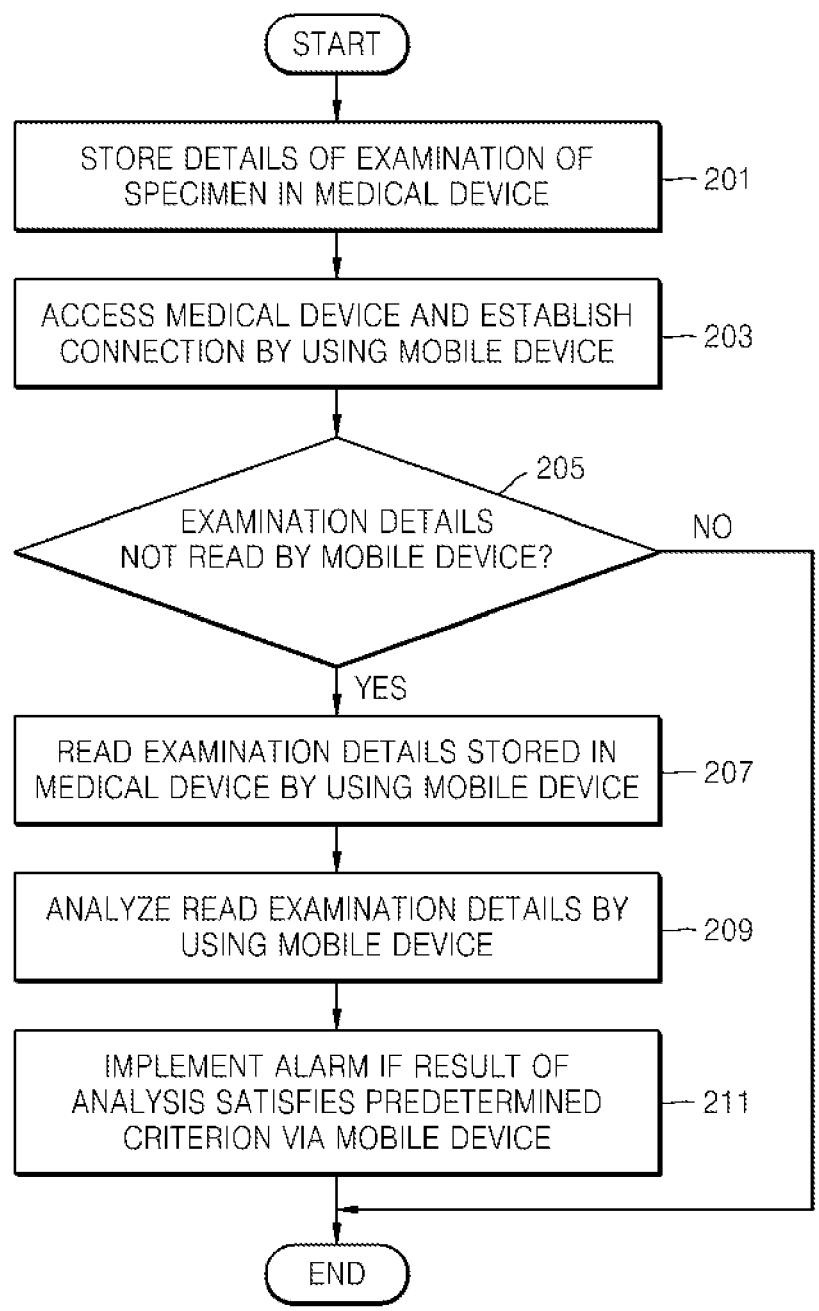
FIG. 2 is a flowchart of a method of implementing an alarm for a medical device through a mobile device, according to an exemplary embodiment.

FIG. 2 is a flowchart of a method of outputting an alarm for a medical device through a mobile device, according to an exemplary embodiment. The method according to the present embodiment includes operations performed by a mobile device 400 of FIG. 4 and a medical device 500 of FIG. 5 in a time series. Thus, although omitted hereinafter, the descriptions with respect to configurations shown in FIGS. 4 and 5 may also apply to the method of FIG. 2.

Details of examination of a sample to be inspected (hereinafter, referred to as a 'specimen') is stored in a medical device (S201). The specimen may generally include various biological tissues that are extracted from an examinee's body. A representative specimen may be the examinee's blood, but is not limited thereto. The specimen may be any specimen other than biological tissue extracted from the examinee as long as it can be inspected by the medical device. The details of examination that are stored in the medical device (hereinafter, referred to as "examination details") may include examination items, examination result values, completion or incompletion of the examination, occurrence of abnormal conditions, and falling within a critical range. The examination details may be stored in a memory installed in the medical device.

The mobile device establishes a connection (Operation 203) with the medical device to have access therewith. The mobile device is connected to the medical device via wired or wireless communication networks such as in-house networks (Local Area Network (LAN) and Wireless Fidelity (WiFi)) or public networks (3G and 4G). The networks are not limited to a particular type of network. The mobile device may connect to the medical device at irregular time intervals according to user manipulation or at every predetermined period set by the user, i.e., user preferences or settings. The connection between the mobile device and the medical device may be maintained only while the mobile device is connected to the medical device to have access therewith and reads the examination details from the medical device. Limiting the duration for the connection between the medical device and the mobile device in this way may prevent the waste of communication resources due to continuously maintaining the connection therebetween. The mobile device may not be connected to only one medical device but may be connected to a plurality of medical devices to have access to the plurality of medical devices. In an exemplary embodiment, the connections may be simultaneous or may not be simultaneous.

The medical device checks a history of the examination details have been read by the mobile device that established a connection therewith and determines whether there are new examination details that have not been read by the mobile device (Operation 205). The medical device may be configured to recognize a plurality of mobile devices and record therein a history of examination details have been read by each of the mobile devices and to allow the mobile device to read only the new examination details that have not been read by the mobile device.

If there are new examination details not read by the mobile device, the mobile device reads the not-read examination details stored in the medical device (Operation 207).

The mobile device analyzes the read examination details (Operation 209). The examination details to be analyzed may include all pieces of information contained in the read examination details, such as examination items, examination result values, completion or incompletion of the examination, occurrence of abnormal conditions, and falling within a critical range.

If the result of analysis of examination details satisfies a predetermined criterion, the mobile device implements an alarm (Operation 211). If the result of analysis satisfies the predetermined criterion, the result of examination of the specimen (hereinafter, referred to as an "examination result") may deviate from a preset range (e. g, occurrence of an abnormal condition or the examination result falling within a critical range), or the examination of the specimen may be completed. If the examination result deviates from the preset range, it may be classified as 'occurrence of a simple abnormal condition' or 'occurrence of a critical condition' according to user's settings. The preset range for the examination result may be individually set for each examination item of an individual examinee.

Figure 12A:
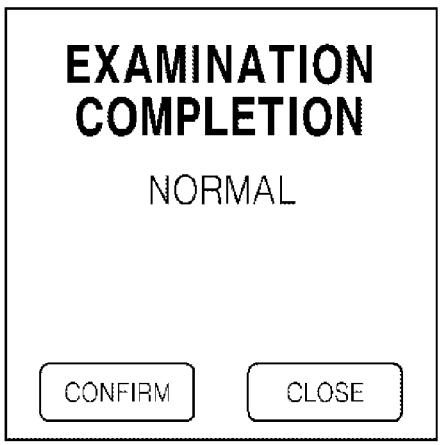
FIGS. 12A through 12D are schematic diagrams of message windows that pop up on a screen of a mobile device when an alarm is implemented as a popup window.
Figure 12B:
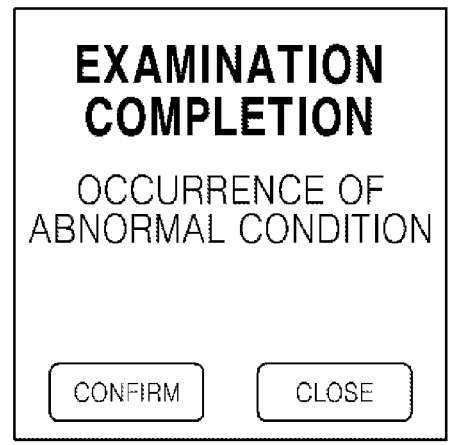
Figure 12C:
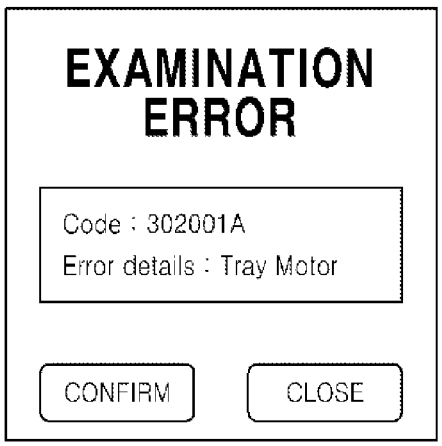
Figure 12D:
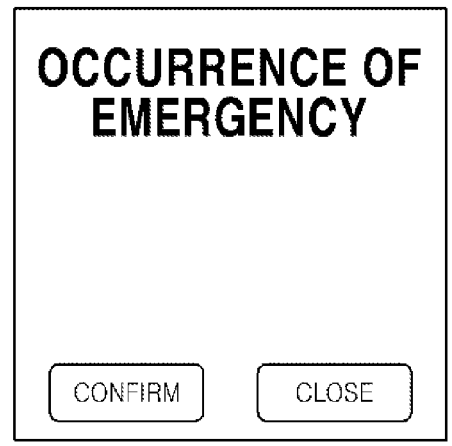

The alarm may be implemented using various ways including a bell sound, music, an acoustic sound, a vibration, flashing light, and a popup window. The alarm may be output in different ways according to situations classified as 'occurrence of a simple abnormal condition' 'occurrence of a critical condition', and 'completion of the examination.' FIGS. 12A through 12D illustrate message windows that pop up on a screen of a mobile device when an alarm is implemented as a popup window. FIGS. 12A and 12B are alarm message windows that pop up on the screen of the mobile device when the examination is normally completed and when an abnormal condition occurs in the examination result, respectively. FIGS. 12C and 12D are alarm message windows that pop up on the screen of the mobile device upon occurrence of an error in a medical device and upon occurrence of an emergency or a critical condition in the examination result, respectively. If the examination result deviates from a preset range to fall within a critical range, an alarm may be output, and at the same time an emergency notification may be transmitted to a predetermined destination such as a hospital emergency room or a fire station. In this case, the emergency notification may be transmitted using various methods such as a Short Message Service (SMS) or an emergency call.

Figure 3:
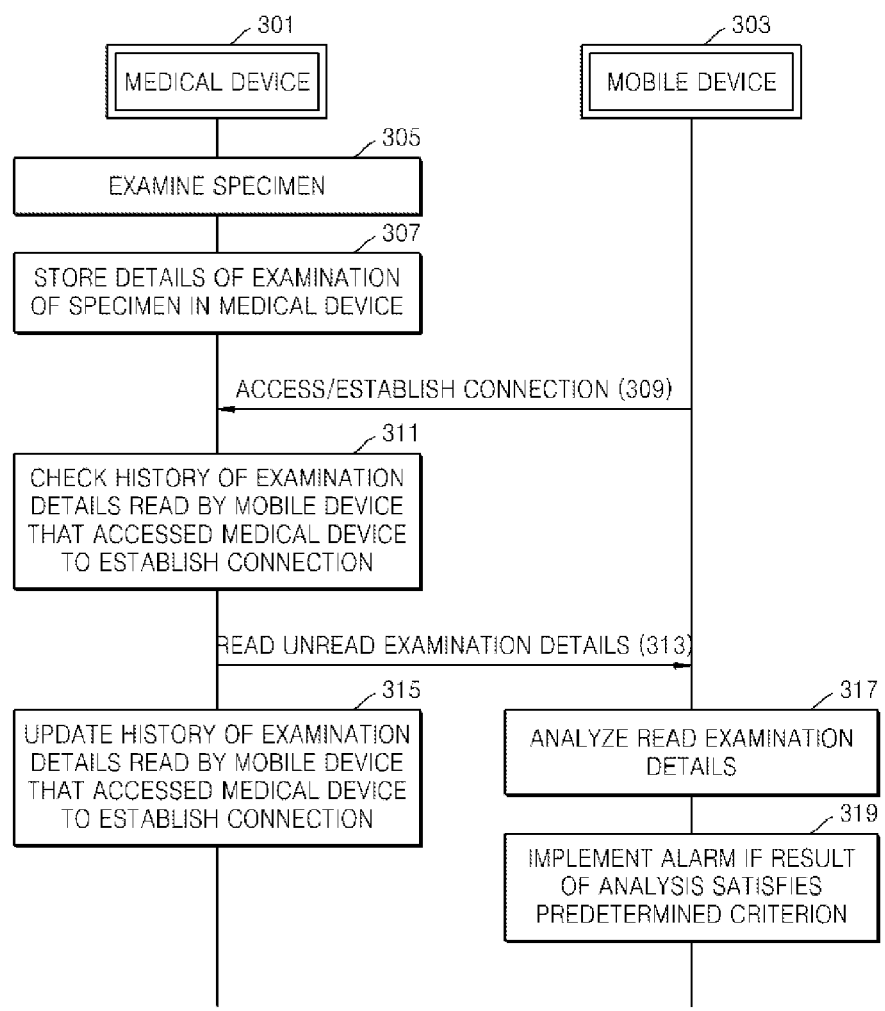
FIG. 3 is a schematic diagram of a system for implementing an alarm for a medical device through a mobile device, according to an exemplary embodiment.

FIG. 3 is a schematic diagram of a system for implementing an alarm for a medical device 301 through a mobile device 303, according to an exemplary embodiment.

Referring to FIG. 3, the medical device 301 performs examination on a specimen (Operation 305) and stores examination details therein (Operation 307). The specimen may generally include various biological tissues that are extracted from an examinee's body. A representative specimen may be the examinee's blood, but is not limited thereto. The specimen may be any specimen other than biological tissue extracted from the examinee as long as it can be inspected by the medical device 301. The stored examination details may include examination items, examination result values, completion or incompletion of the examination, occurrence of abnormal conditions, and falling within a critical range. The examination details may be stored in a memory installed in the medical device 301.

The mobile device 303 has set up the connection to the medical device 301 to have access therewith (Operation 309). The mobile device 303 accesses and is connected to the medical device 301 via wired or wireless communication networks such as in-house networks (LAN and WiFi) or public networks (3G and 4G). The networks are not limited to a particular type of network. The mobile device may connect to the medical device at irregular time intervals according to user manipulation or at every predetermined period set by the user. The connection between the mobile device 303 and the medical device 301 may be maintained only while the mobile device 303 accesses the medical device to obtain information therefrom and reads the examination details from the medical device 301. Limiting the duration for the connection between the medical device 301 and the mobile device 303 in this way may prevent the waste of communication resources due to continuously maintaining the connection therebetween. The mobile device 303 may not be connected to only one medical device but may be connected to a plurality of medical devices to access therewith.

The medical device 301 checks a history of the examination details that are read by the mobile device 303 that established a connection therewith, and determines whether there are new examination details that are not read by the mobile device 303 (Operation 311). The medical device 301 may be configured to recognize a plurality of mobile devices and record therein a history that examination details have been read by each of the mobile devices and to allow the mobile device to read only the new examination details that have not been read by the mobile device.

If there are new examination details not read by the mobile device 303, the mobile device 303 reads the unread examination details stored in the medical device 301 (Operation 313).

The medical device 301 updates a history of examination details read by the mobile device 303 (Operation 315). In other words, the medical device 301 changes the read examination details from a not-read status to a read status.

The mobile device 303 analyzes the read examination details (Operation 317). The examination details to be analyzed may include all pieces of information contained in the read examination details, such as examination items, examination result values, completion or incompletion of the examination, occurrence of abnormal conditions, and falling within a critical range.

If the result of analysis of examination details satisfies a predetermined criterion, the mobile device outputs an alarm (Operation 319). If the result of analysis satisfies the predetermined criterion, the examination result may deviate from a preset range (e. g, occurrence of an abnormal condition, or the examination result falling within a critical range), or the examination of the specimen may be completed. If the examination result deviates from the preset range, it may be classified as 'occurrence of a simple abnormal condition' or 'occurrence of a critical condition' according to user's settings. The preset range for the examination result may be individually set for each examination item of an individual examinee.

The alarm may be implemented using various ways including a bell sound, music, an acoustic sound, a vibration, flashing light, and a popup window. The alarm may be output in different ways according to situations classified as 'occurrence of a simple abnormal condition' 'occurrence of a critical condition', and 'completion of the examination,' as shown in FIGS. 12A through 12D that illustrate message windows that pop up on a screen of a mobile device when an alarm is implemented as a popup window. FIGS. 12A and 12B are alarm message windows that pop up on the screen of the mobile device when the examination is normally completed and when an abnormal condition occurs in the examination result, respectively. FIGS. 12C and 12D are alarm message windows that pop up on the screen of the mobile device upon occurrence of an error in a medical device and upon occurrence of an emergency/a critical condition in the examination result, respectively. If the examination result deviates from a preset range to fall within a critical range, an alarm may be output, and an emergency notification may also be transmitted to a predetermined destination such as a hospital emergency room or a fire station. In this case, the emergency notification may be transmitted using various methods such as an SMS or an emergency call.

Figure 4:
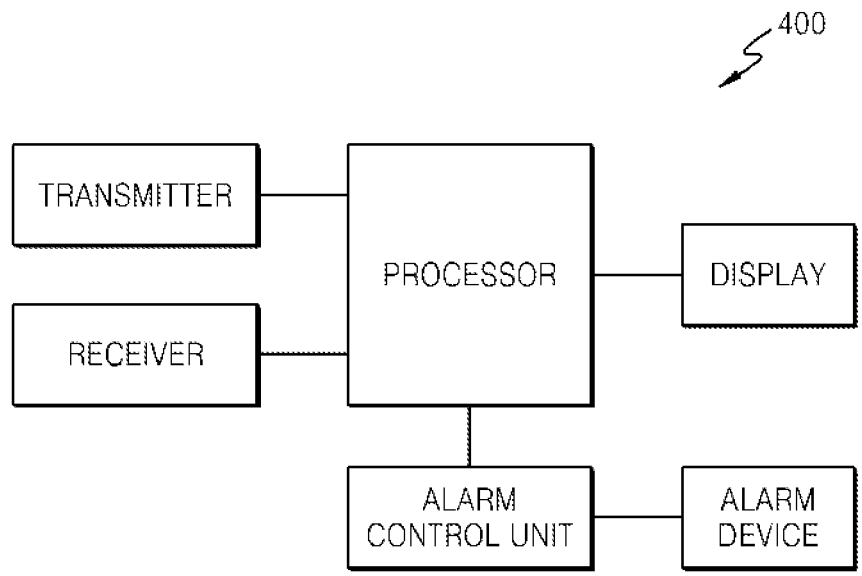
FIG. 4 is a schematic diagram of a mobile device through which an alarm for a medical device is implemented, according to an exemplary embodiment.

FIG. 4 is a schematic diagram of a mobile device 400 through which an alarm for a medical device is output, according to an exemplary embodiment. The mobile device 400 according to the present embodiment includes a processor, a transmitter, a receiver, an alarm control unit, an alarm device, and a display. All of the aforementioned components of the mobile device may be implemented as hardware components. In other exemplary embodiments, some of the aforementioned components may be implemented as software components or software modules.

The transmitter transmits to the medical device requests for establishing a connection with the medical device and for reading details of examination of a specimen (hereinafter, referred to as "examination details") stored in the medical device. The requests are made via wired or wireless communication networks such as in-house networks (LAN and WiFi) or public networks (3G and 4G). The networks are not limited to a particular type of network. When necessary, the requests may be made through a connection between the mobile device 400 and the medical device via Bluetooth. The request for establishing a connection with the medical device may be transmitted at irregular time intervals according to user manipulation or at every predetermined period set by the user. The requested connection may be maintained only while the mobile device 400 establishes a connection with the medical device and receives the examination details therefrom. Limiting the duration for the connection between the medical device and the mobile device 400 in this way may prevent the waste of communication resources due to continuously maintaining the connection therebetween. The mobile device 400 may not be connected to only one medical device but may be connected to a plurality of medical devices to access therewith. In other words, the mobile device 400 may transmit a request for establishing a connection to the plurality of medical devices.

The receiver receives a response to accept the request for establishing a connection with the medical device and the examination details from the medical device. When the response is received from the medical device, a connection between the mobile device 400 and the medical device is established, and the examination details are received through the connection therebetween.

The processor analyzes the examination details and determines whether the result of analysis of the examination details satisfies a predetermined criterion. The examination details to be analyzed may include all pieces of information contained in the read examination details, i.e., examination items, examination result values, completion or incompletion of the examination, occurrence of abnormal conditions, falling within a critical range, etc. If the result of analysis satisfies a predetermined criterion, the examination result may deviate from a preset range (e.g., occurrence of an abnormal condition, or the examination result falling within a critical range), or the examination of the specimen may be completed. If the examination result deviates from the preset range, it may be classified as 'occurrence of a simple abnormal condition' or 'occurrence of a critical condition' according to user's settings. The preset range for the examination result may be individually set for each examination item of an individual examinee. The processor may be configured to allow the mobile device 400 to read only examination details that have not been read by the mobile device. If there are examination details not read by the mobile device, the mobile device 400 reads the unread examination details stored in the medical device.

When the result of analysis satisfies the predetermined criterion, the alarm control unit implements an alarm through an alarm device. The alarm may be implemented using various ways including a bell sound, music, an acoustic sound, a vibration, flashing light, and a popup window. The alarm may be output in different ways according to situations classified as 'occurrence of a simple abnormal condition' occurrence of a critical condition', and 'completion of the examination,' as shown in FIGS. 12A through 12D that illustrate message windows that pop up on a screen of a mobile device when an alarm is implemented as a popup window. If the examination result deviates from a preset range to fall within a critical range, an alarm may be output, and an emergency notification may also be transmitted to a predetermined destination such as a hospital emergency room or a fire station. In this case, the emergency notification may be transmitted using various methods such as an SMS or an emergency call.

The display may display a user interface related to an alarm for the medical device and information about a progress of examination of a specimen.

Figure 5:
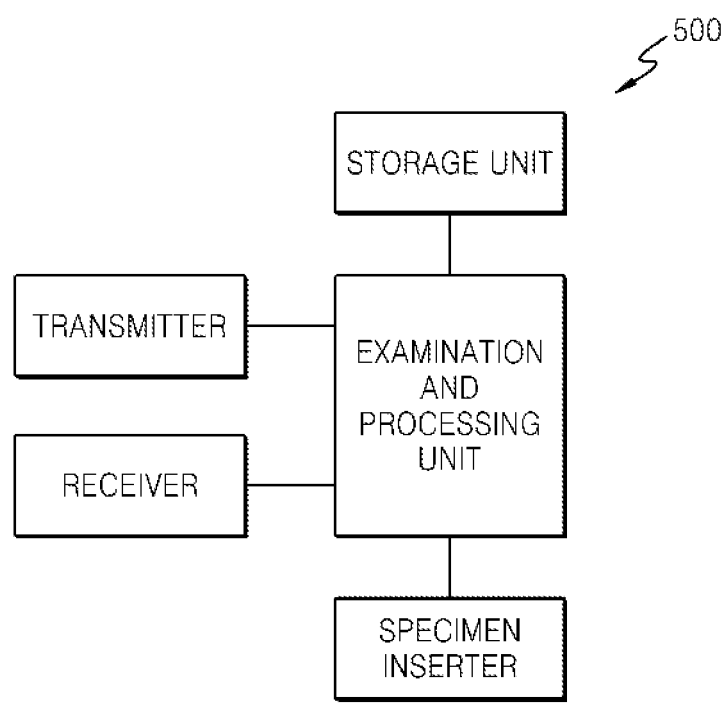
FIG. 5 is a schematic diagram of a medical device for implementing an alarm through a mobile device, according to an exemplary embodiment.

FIG. 5 is a schematic diagram of a medical device 500 for implementing an alarm through a mobile device, according to an exemplary embodiment. Referring to FIG. 5, the medical device 500 according to the present embodiment includes a specimen inserter, an examination and processing unit, a storage unit, a receiver, and a transmitter. As with the exemplary embodiment described in FIG. 4, each of these components may be implemented in hardware or software.

The specimen inserter is configured to insert a specimen to be inspected. The specimen may generally include various biological tissues that are extracted from an examinee's body. A representative specimen may be the examinee's blood, but is not limited thereto. The specimen may be any specimen other than biological tissue extracted from the examinee as long as it can be inspected by the medical device 500.

The examination and processing unit performs examination of a specimen in the same manner that medical examination equipment generally performs and processes the examination result. The examination result means details of the examination including examination items, examination result values, completion/incompletion of the examination, occurrence of abnormal conditions, and falling within a critical range, and is symmetrically arranged and processed. The examination and processing unit may be configured to recognize a plurality of mobile devices and record therein a history that the examination details have been read by each of the mobile devices and to allow the mobile device to read only new examination details that have not been read by the mobile device. In other words, if there are new examination details not read by the mobile device, the mobile device is allowed to read the unread examination details stored in the medical device 500.

The storage unit stores the examination result processed by the examination and processing unit.

The receiver receives requests for establishing a connection with the medical device 500 and for reading examination details. The requests may be received via wired or wireless communication networks such as in-house networks (LAN and WiFi) or public networks (3G and 4G). The networks are not limited to a particular type of network. When necessary, the requests may be received through a connection between the mobile device and the medical device 500 via Bluetooth. The request for establishing a connection with the medical device may be transmitted at irregular time intervals according to user manipulation or at every predetermined period set by the user. The requested connection may be maintained only while the mobile device establishes a connection with the medical device 500 and receives the examination details therefrom. Limiting the duration for the connection between the medical device and the mobile device 400 in this way may prevent the waste of communication resources due to continuously maintaining the connection therebetween. The medical device 500 may not be connected to only one mobile device but establish a plurality of connections with a plurality of mobile devices. Alarms may be set differently across a plurality of mobile devices that are connected to the medical device 500, thereby allowing different settings and notifications of alarms in response to the same examination result, as needed by a diagnostic staff (or a user of a mobile device).

The transmitter transmits to the mobile device a response that accepts a request for establishing a connection with the medical device 500 together with examination details. When the mobile device receives the response from the medical device 500, a connection between the mobile device and the medical device 500 is established, and the examination details are transmitted through the connection therebetween. In this case, the examination details include examination result defined as particular values or ranges of values. If the examination result deviates from a preset range to fall within a critical range, the transmitter may transmit an emergency notification to a predetermined destination such as a hospital emergency room or a fire station. In this case, the emergency notification may be transmitted using various methods such as an SMS or an emergency call.

Upon receipt of the examination details from the medical device 500, the mobile device analyzes the examination details and implements an alarm if the result of analysis satisfies a predetermined criterion. The alarm may be implemented using various ways including a bell sound, music, an acoustic sound, a vibration, flashing light, and a popup window. The alarm may be output in different ways according to situations classified as 'occurrence of a simple abnormal condition' 'occurrence of a critical condition', and 'completion of the examination,' as shown in FIGS. 12A through 12D that illustrate message windows that pop up on a screen of a mobile device when an alarm is implemented as a popup window. If the examination result deviates from a preset range to fall within a critical range, an alarm may be output, and an emergency notification may also be transmitted to a predetermined destination such as a hospital emergency room or a fire station. In this case, the emergency notification may be transmitted using various methods such as an SMS or an emergency call.

Figure 6:
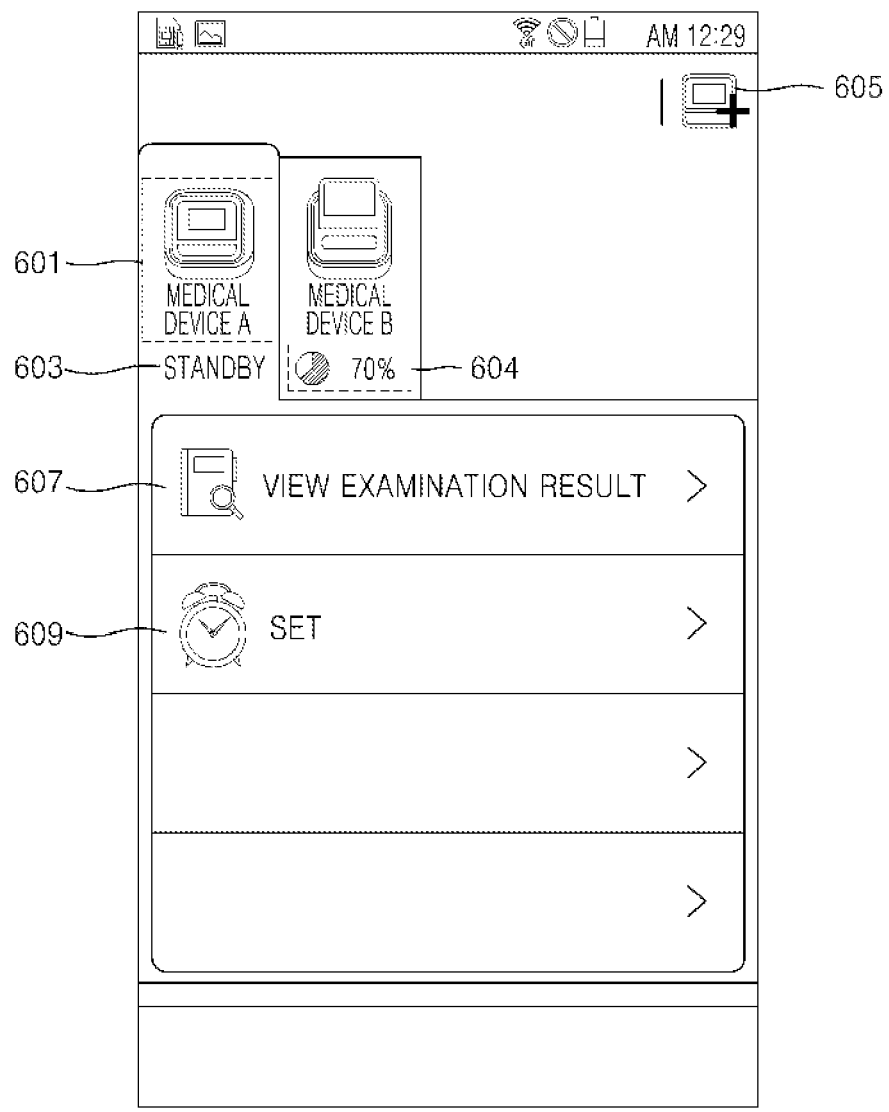
FIG. 6 is a schematic diagram of a screen of a mobile device on which a medical device alarm application runs, according to an exemplary embodiment.

FIG. 6 is a schematic diagram of a screen of a mobile device on which a medical device alarm application runs, according to an exemplary embodiment.

The mobile device may establish connections with a plurality of medical devices. In the present exemplary embodiment, the mobile device currently establishes connections with two medical devices (medical device A and medical device B). The medical devices A and B may be distinguished by their corresponding icons and a reference numeral 601. In addition, current statuses 603 and 604 of the medical device A 601 and the medical device B may be displayed. Although the medical device A 601 is currently in a standby status, the current status 603 of the medical device A 601 may be an off status or a disconnected status, or may be represented in various other ways such as a rate of progress of examination. According to the present embodiment, the current status 604 of the medical device B is an in-progress status and represents an examination progress rate of 70%. When the medical apparatus A is selected by using various control methods, e.g., by a user touching the screen, pressing a button, and moving a cursor, items 'view examination results' and 'set' 607 and 609 for the medical apparatus A are displayed on the screen. In addition, a registered or unregistered medical device list or a button 605 for registering an unregistered medical device may be displayed on the screen.

Figure 7:
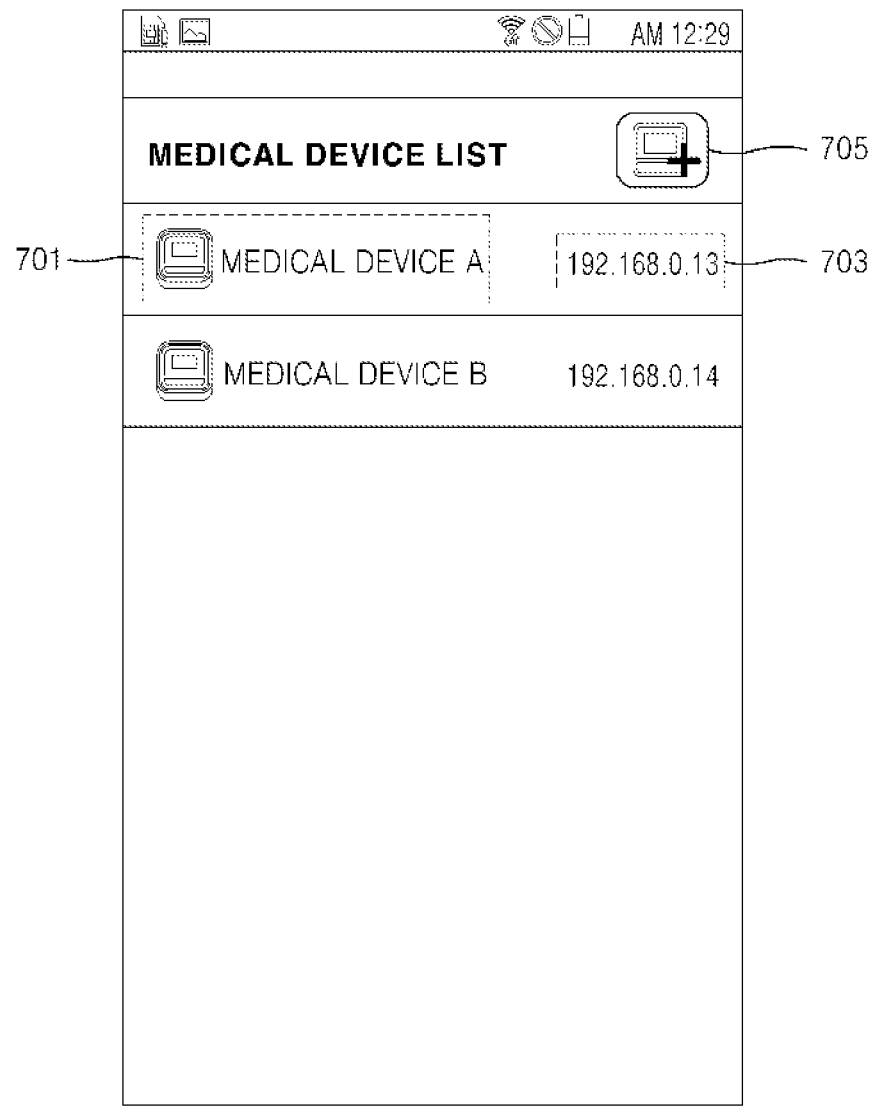
FIG. 7 is a schematic diagram of a screen of a mobile device that displays a medical device list or appears when a button for registering an unregistered medical device is selected, according to an exemplary embodiment.

FIG. 7 is a schematic diagram of a screen of a mobile device that displays a medical device list or appears when the button 605 shown in FIG. 6 for registering an unregistered medical device is selected, according to an exemplary embodiment. Medical devices A and B connected to the mobile device are distinguished by their corresponding icons and reference numeral 701 and displayed on the medical device list together with IP addresses 703 thereof. In addition, a separate button 705 for registering an unregistered medical device may be displayed on the screen. When the separate button 705 is selected by various control methods, e.g., by a user touching the screen, pressing a button, and moving a cursor, a list of unregistered medical devices that are connectable to the mobile device may be displayed on the screen. When the user selects a desired medical device from the list for registration, the selected medical device may be added to the medical device list so that it may be registered together with the medical devices A and B.

FIG. 8 is a schematic diagram of a screen of a mobile device that appears when an item 'view examination results' shown in FIG. 6 is selected, according to an exemplary embodiment. An examination result list may be displayed on the screen so that examination results 1 through 8 in the examination result list are arranged in reverse chronological order (most recent examination at the top of the list) or in other ways. An item 801 indicating each of the examination results 1 through 8 may be displayed together with date and time 803 of examination.

FIG. 9 is a schematic diagram of a screen of a mobile device that appears when 'examination result 8' shown in FIG. 8 is selected, according to an exemplary embodiment. Referring to FIG. 9, an examination result item 901 may include examination items 903, examination result values 905, and normal reference ranges 907. According to the examination result values 905, an alarm range indicator 909 and a critical range indicator 911 may be added. In the exemplary embodiment shown in FIG. 9, the examination items 903 such as Albumin (ALB), Total Protein (TP), Cholesterol (CHOL), Glucose (GLU), Blood Urea Nitrogen (BUN), and High-Density Lipoprotein (HDL) are indicated as having an alarm range value, and the examination item 903 such as BUN is indicated as having a critical range value.

Examination items 903 may include, but not limited to, ALB, Alkaline Phosphatase (ALP), ALT (Alanine Aminotransferase), Amylase (AMY), Aspartate Aminotransferase (AST), BUN, CHOL, Creatine Kinase (CK), Creatinine (CRE), Direct Bilirubin (DBIL), Total Bilirubin (TBIL), GLU, Hemoglobin A1c (HbA1c), HDL, Prostate Specific Antigen (PSA), Troponin I (TnI), and Brain Natriuretic Peptide (BNP). The examination items 903 may also include other various items that can be inspected by a medical device without limitation.

FIGS. 10A through 10C are schematic diagrams of screens of a mobile device that appear when the item 'set' 609 shown in FIG. 6 is selected, according to an exemplary embodiment.

FIG. 10A illustrates a screen for setting an alarm upon selection of the item 'set' 609 shown in FIG. 6. The alarm may be set to be output upon completion of examination 1001, upon occurrence of an abnormal condition 1003 (falling out of a preset range), and when a BUN value falls within a critical range 1005. The alarm for each menu item 1001, 1003, or 1005 may be set to be output according to whether a check box next to the item 1001, 1003, or 1005 is checked. By selecting a button 1007, a critical range for a particular examination item may be additionally set.

Upon selection of the button 1007, a screen of the mobile device shown in FIG. 10B is displayed. For example, if a critical range for ALT value is set, the type of an acoustic sound or activation of a vibration may be selected, and the critical range for ALT value may be directly determined and entered by a user. When a button 1015 for selecting the type of acoustic sound is pressed, an acoustic sound selection window with a plurality of acoustic sounds listed is displayed in a popup window on the screen, and a desired acoustic sound is selected as an alarm by the user in various ways, e.g. by touching the screen, pressing a button, and moving a cursor. Similarly, when a button 1017 for selecting an examination item whose critical range will be set is pressed, an examination item selection window with a plurality of examination items listed is displayed in a popup window on the screen, and a desired examination item is selected by the user in various ways, e.g. by touching the screen, pressing a button, and moving a cursor. A numeric pad 1019 may also be displayed to allow the user to directly enter a value. When the critical range for ALT value is set by performing the above process, item ALT 1021 may be added to the screen for setting an alarm shown in FIG. 10A and displayed as shown in FIG. 10C.

Figure 11:
FIG. 11 is a schematic diagram of a screen of a mobile device that displays an alarm status list, according to an exemplary embodiment.

FIG. 11 is a schematic diagram of a screen of a mobile device that displays an alarm status list, according to an exemplary embodiment.

A current alarm status that is read by the mobile device from medical devices (medical devices A and B) may be displayed as an alarm status list shown in FIG. 11. The current alarm status list may be arranged in reverse chronological order by placing alarm items in order from most recently outputted alarms (i.e., the latest alarm at the top of the list), or in the opposite order. Alarm items may be classified by an icon 1101 indicating completion of examination, an icon 1105 indicating occurrence of an abnormal condition, and an icon 1107 indicating occurrence of an emergency. Each of the alarm items may include identification (ID) information 1103 about a medical device that has transmitted an alarm, ID information 1109 about an examinee, and date and time 1111 when the alarm is output.

The above methods according to the embodiments of the present invention can be recorded as programs that can be executed on a computer and be implemented through general-purpose digital computers which can run the programs using a computer-readable recording medium. Data structures described in the above method can also be recorded on a computer-readable recording medium in a variety of ways. Program storage devices that can be used to describe a storage device containing computer codes executable to perform various methods according to the present invention are not understood to include transitory media such as carrier waves or signals. Examples of the computer-readable recording medium include recording media, such as magnetic storage media (e.g., ROM, floppy disks, hard disks, etc.), and optical recording media (e.g., CD-ROMs or DVDs).

While one or more embodiments of the present invention have been described with reference to the figures, it will be understood by one of ordinary skill in the art that various changes in form and details may be made therein without departing from the spirit and scope of the present invention as defined by the following claims. Thus, it should be understood that the exemplary embodiments described therein should be considered in a descriptive sense only and not for purposes of limitation. The scope of the invention is defined not by the detailed description of the invention but by the appended claims, and all differences within the scope of the appended claims and their equivalents will be construed as being included in the present invention.

What is claimed is:

1. A method of providing a notification by a mobile device, the method comprising:
 establishing a connection between the mobile device and a medical device;
 reading a result of examination of a specimen from the medical device at predetermined periods of time;
 setting a plurality of criteria to provide the notification about the result of the examination;
 determining whether the result of the examination satisfies at least one criterion of the plurality of criteria; and
 outputting the notification in response to the result of the examination satisfying the at least one criterion,
 wherein a corresponding notification is set differently for each of the plurality of criteria, and the corresponding notification comprises any one or any combination of a sound, a vibration, and a visual display element.

2. The method of claim 1, further comprising maintaining the connection only while the mobile device reads the result of examination information from the medical device.

3. The method of claim 1, wherein the determining comprises determining that the result of the examination satisfies the at least one criterion of the plurality of criteria when the result of the examination of the specimen deviates from a preset range and falls within a critical range.

4. The method of claim 3, further comprising providing a list of a plurality of medical devices that are distinguished by an icon or an identifier.

5. A mobile device comprising:
 a communication interface configured to communicate with a medical device;
 a processor configured to:
  establish a connection with the medical device to read a result of examination of a specimen at predetermined periods of time;
  set a plurality of criteria to provide a notification about the result of the examination; and
  determine whether the result of the examination satisfies at least one criterion of the plurality of criteria; and
 an output device configured to output a notification in response to the result of the examination satisfying the at least one criterion
 wherein a corresponding notification is set differently for each of the plurality of criteria, and the corresponding notification comprises any one or any combination of a sound, a vibration, and a visual display element.

6. The mobile device of claim 5, wherein the processor is further configured to control the communication interface to maintain the connection only while the mobile device establishes the connection with the medical device and receives the results of the examination from the medical device.

7. The mobile device of claim 5, wherein when the result of the examination of the specimen deviates from a preset range and falls within a critical range, the processor determines that the result of the examination satisfies the at least one criterion of the plurality of criteria.

8. The mobile device of claim 7, wherein the medical device provides a list of a plurality of medical devices that is distinguished by an icon or an identifier.

9. A non-transitory computer readable storage medium storing a program that is executable by a computing device to perform a method comprising:
 establishing a connection between the computing device and a medical device;
 reading a result of examination of a specimen from the medical device at predetermined periods of time;
 setting a plurality of criteria to provide a notification about the result of the examination;
 determining whether the result of the examination satisfies at least one criterion of the plurality of criteria; and controlling the computing device to output the notification in response to the result of the examination satisfying the at least one criterion,
wherein a corresponding notification is set differently for each of the plurality of criteria, and the corresponding notification comprises any one or any combination of a sound, a vibration, and a visual display element.

10. The non-transitory computer readable storage medium of claim 9, further comprising maintaining the only while the mobile device establishes the connection with the medical device and receives the examination result from the medical device.

11. The non-transitory computer readable storage medium of claim 9, wherein the determining comprises determining that the result of the examination satisfies the at least one criterion of the plurality of criteria when the result of the examination deviates from a preset range and falls within a critical range.

12. The non-transitory computer readable storage medium of claim 11, wherein the method further comprising providing a list of a plurality of medical devices that are distinguished by an icon or an identifier.

13. The method of claim 1, further comprising:
displaying information by the mobile device on a screen, wherein the information is about a current status of the medical device that is received from the medical device.

14. The method of claim 13, wherein the current status is at least one from among a standby status, an off status, a disconnected status, and an examination in-progress status.

15. The method of claim 14, wherein examination history is represented by displaying information of the examination history on the screen by a percentage value or a graphical representation.

16. The method of claim 1, further comprising:
receiving an input that selects a type of the notification; and
outputting the notification with the selected type.

17. The non-transitory computer readable storage medium of claim 9, wherein the method further comprises receiving an input that selects a type of the notification, and controlling the mobile device to output the notification with the selected type.

* * * * *